(12) United States Patent
Itoh et al.

(10) Patent No.: US 6,815,531 B1
(45) Date of Patent: Nov. 9, 2004

(54) TUMOR ANTIGEN PROTEINS, GENES THEREOF, AND TUMOR ANTIGEN PEPTIDES

(75) Inventors: Kyogo Itoh, 2-25-9, Keyaki-dai, Kiyama-cho, Miyaki-gun, Saga-ken (JP); Shigeki Shichijo, Kurume (JP); Yasuhisa Imai, Kurume (JP)

(73) Assignee: Kyogo Itoh, Saga-ken (JP)

( * ) Notice: Subject to any disclaimer, the term of this patent is extended or adjusted under 35 U.S.C. 154(b) by 0 days.

(21) Appl. No.: 09/202,047

(22) PCT Filed: Jun. 4, 1997

(86) PCT No.: PCT/JP97/01893

§ 371 (c)(1),
(2), (4) Date: Dec. 7, 1998

(87) PCT Pub. No.: WO97/46676

PCT Pub. Date: Dec. 11, 1997

(30) Foreign Application Priority Data

Jun. 7, 1996 (JP) .............................................. 8-168429
Aug. 10, 1996 (JP) .............................................. 8-287572
Nov. 25, 1996 (JP) .............................................. 8-330424

(51) Int. Cl.$^7$ .............................................. C07K 14/00
(52) U.S. Cl. ........................ 530/350; 530/327; 530/328
(58) Field of Search ................................. 530/350, 800, 530/328, 327; 536/23.1; 514/2

(56) References Cited

U.S. PATENT DOCUMENTS 5,776,677 A * 7/1998 Tsui et al.

FOREIGN PATENT DOCUMENTS

WO    WO95/34579    12/1995

OTHER PUBLICATIONS

Gura Science, v278, 1997, pp. 1041–1042.*
Tait et al. Clin.Canc.Res., vol. 5, Jul. 1999, pp. 1708–1714.*
Crystal, R.G. Science, vol. 270, Oct. 1995, pp. 404–410.*
Boon Adv Can Res, 1992, 58:177–210.*
Spitler Cancer Biotherapy, 1995, 10:1–3.*
Ezzell J. NIH Res, 1995, 7:46–49.*
Stenesh, Dictionary of Biochemistry and Molecular Biology, Second Edition, John Wiley and Sons, p. 118 and 383, 1989.*
Lin et al., Biochemistry 14:1559–1563, 1975.*
Schwartz et al., Proc. Natl. Acad. Sci. USA 84:6408–6411, 1987.*
Burgess et al., The Journal of Cell Biology 111:2129–2138, 1990.*
Lazar et al., Molecular and Cellular Biology 8:1257–1252, 1988.*
M. Nakao et al., "HLA A2601–Restricted CTLS 1–15 Recognize A Peptide Antigen Expression Squamous Cell Carcinoma", Cancer Research, vol. 55, (Oct. 1, 1995), pp. 4248–4252. (XP–002922826).
S. Shichijo et al., "A Gene Encoding Antigenic Peptides of Human Squamous Cell Carcinoma Recognized by Cytotoxic T Lymphocytes", The Journal of Experimental Medicine, vol. 187, No. 3, (Feb. 2, 1998), pp. 277–288. (XP–002948570).
D. Kraft et al., "Human ara Kb beta–galactosidase fusion protein coding sequence", EMBL Database accession No. AAt09256, (Sep. 30, 1996). (XP–002209538).
D. Kraft et al., "Human ara Kb beta–galactosidase fusion protein." EMBL Database accession No. AAR88069, (Sep. 26, 1996). (XP–002209385).
J. Exp. Med., vol. 183, (1996), T. Boon et al.; "Human Tumor Antigens Recognized by T Lymphocytes", p. 725–729.
T. Boon et al., J. Exp. Med., vol. 183, pp. 725–729 (Mar. 1996).
P. van der Bruggen et al., Science, vol. 254, pp. 1643–1647 (Dec. 1991).
Y. Kawakami et al., Proc. Natl. Acad. Sci. USA, vol. 91, pp. 6458–6462 (Jul. 1994).
Y. Kawakami et al., Proc. Natl. Acad. Sci. USA, vol. 91, pp. 3515–3519 (Apr. 1994).
Y. Kawakami et al., J. Exp. Med., vol. 180, pp. 347–352 (Jul. 1994).
C. Traversari et al., J. Exp. Med., vol. 176, pp. 1453–1457 (Nov. 1992).
T. Wölfel et al., Eur. J. Immunol., vol. 24, pp. 759–764 (1994).
M. Nakao et al., Cancer Research, vol. 55, pp. 4248–4252 (Oct. 1995).
D. D. Kharkevitch et al., Int. J. Cancer, vol. 58, pp. 317–323 (1994).
H. G. Rammensee et al., Immunogentics, vol. 41, pp. 178–228 (1995).
R. T. Kubo et al., J. Immunol., vol. 152, pp. 3913–3924 (1994).
W. M. Kast et al., Immunol., vol. 152, pp. 3904–3912 (1994).
A. Kondo et al., J. Immunol., vol. 155, pp. 4307–4312 (1995).

* cited by examiner

Primary Examiner—Larry R. Helms
(74) Attorney, Agent, or Firm—Birch, Stewart, Kolasch & Birch, LLP (57) ABSTRACT

DNA encoding a protein having the amino acid sequence shown in SEQ ID NO: 2 or a variant protein thereof in which one or more amino acid residues are substituted, deleted or added, said protein or variant protein thereof being capable of yielding, through its intracellular decomposition, peptide fragment(s) which can bind to major histocompatibility complex (MHC) class I antigen and which can be recognized by T cells in such binding state, medicines comprising said DNA as an active ingredient, expression plasmids comprising said DNA, transformants transformed with said expression plasmids, as well as tumor antigen proteins and tumor antigen peptides produced by expression of said DNA.

4 Claims, 1 Drawing Sheet

SEQUENCE LISTING

<160> NUMBER OF SEQ ID NOS: 2

<210> SEQ ID NO 1
<211> LENGTH: 2527
<212> TYPE: DNA
<213> ORGANISM: Homo sapiens
<220> FEATURE:
<221> NAME/KEY: misc_feature
<222> LOCATION: (1)..(2527)
<223> OTHER INFORMATION: Strandedness: Double-stranded
<220> FEATURE:
<221> NAME/KEY: 5'UTR
<222> LOCATION: (1)..(38)
<220> FEATURE:
<221> NAME/KEY: CDS
<222> LOCATION: (39)..(2438)
<220> FEATURE:
<221> NAME/KEY: 3'UTR
<222> LOCATION: (2439)..(2506)
<220> FEATURE:
<221> NAME/KEY: polyA_site
<222> LOCATION: (2507)..(2527)

<400> SEQUENCE: 1

```
ggttcggcgg cagccgggct cggagtggac gtgccact atg ggg tcg tcc aag aag      56
                                         Met Gly Ser Ser Lys Lys
                                           1               5 cat cgc gga gag aag gag gcg gcc ggg acg acg gcg gcg gcc ggc acc       104
His Arg Gly Glu Lys Glu Ala Ala Gly Thr Thr Ala Ala Ala Gly Thr
             10                  15                  20 ggg ggt gcc acc gag cag ccg ccg cgg cac cgg gaa cac aaa aaa cac       152
Gly Gly Ala Thr Glu Gln Pro Pro Arg His Arg Glu His Lys Lys His
         25                  30                  35 aag cac cgg agt ggc ggc agt ggc ggt agc ggt ggc gaa cga cgg aag       200
Lys His Arg Ser Gly Gly Ser Gly Gly Ser Gly Gly Glu Arg Arg Lys
     40                  45                  50 cgg agc cgg gaa cgt ggg ggc gag cgc ggg agc ggg cgg cgc ggg gcc       248
Arg Ser Arg Glu Arg Gly Gly Glu Arg Gly Ser Gly Arg Arg Gly Ala
 55                  60                  65                  70 gaa gct gag gcc cgg agc agc acg cac ggg cgg gag cgc agc cag gca       296
Glu Ala Glu Ala Arg Ser Ser Thr His Gly Arg Glu Arg Ser Gln Ala
                 75                  80                  85 gag ccc tcc gag cgg cgc gtg aag cgg gag aag cgc gat gac ggc tac       344
Glu Pro Ser Glu Arg Arg Val Lys Arg Glu Lys Arg Asp Asp Gly Tyr
             90                  95                 100 gag gcc gct gcc agc tcc aaa act agc tca ggc gat gcc tcc tca ctc       392
Glu Ala Ala Ala Ser Ser Lys Thr Ser Ser Gly Asp Ala Ser Ser Leu
         105                 110                 115 agc atc gag gag act aac aaa ctc cgg gca aag ttg ggg ctg aaa ccc       440
Ser Ile Glu Glu Thr Asn Lys Leu Arg Ala Lys Leu Gly Leu Lys Pro
     120                 125                 130 ttg gag gtt aat gcc atc aag aag gag gcg ggc acc aag gag gag ccc       488
Leu Glu Val Asn Ala Ile Lys Lys Glu Ala Gly Thr Lys Glu Glu Pro
135                 140                 145                 150 gtg aca gct gat gtc atc aac cct atg gcc ttg cga cag cga gag gag       536
Val Thr Ala Asp Val Ile Asn Pro Met Ala Leu Arg Gln Arg Glu Glu
                155                 160                 165 ctg cgg gag aag ctg gcg gct gcc aag gag aag cgc ctg ctg aac caa       584
Leu Arg Glu Lys Leu Ala Ala Ala Lys Glu Lys Arg Leu Leu Asn Gln
            170                 175                 180 aag ctg ggg aag ata aag acc cta gga gag gat gac ccc tgg ctg gac       632
Lys Leu Gly Lys Ile Lys Thr Leu Gly Glu Asp Asp Pro Trp Leu Asp
        185                 190                 195
```

```
gac act gca gcc tgg atc gag agg agc cgg cag ctg cag aag gag aag     680
Asp Thr Ala Ala Trp Ile Glu Arg Ser Arg Gln Leu Gln Lys Glu Lys
    200                 205                 210 gac ctg gca gag aag agg gcc aag tta ctg gag gag atg gac caa gag     728
Asp Leu Ala Glu Lys Arg Ala Lys Leu Leu Glu Glu Met Asp Gln Glu
215                 220                 225                 230 ttt ggt gtc agc act ctg gtg gag gag gag ttc ggg cag agg cgg cag     776
Phe Gly Val Ser Thr Leu Val Glu Glu Glu Phe Gly Gln Arg Arg Gln
                235                 240                 245 gac ctg tac agt gcc cgg gac ctg cag ggc ctc acc gtg gag cat gcc     824
Asp Leu Tyr Ser Ala Arg Asp Leu Gln Gly Leu Thr Val Glu His Ala
        250                 255                 260 att gat tcc ttc cga gaa ggg gag aca atg att ctt acc ctc aag gac     872
Ile Asp Ser Phe Arg Glu Gly Glu Thr Met Ile Leu Thr Leu Lys Asp
            265                 270                 275 aaa ggc gtg ctg cag gag gag gag gac gtg ctg gtg aac gtg aac ctg     920
Lys Gly Val Leu Gln Glu Glu Glu Asp Val Leu Val Asn Val Asn Leu
    280                 285                 290 gtg gat aag gag cgg gca gag aaa aat gtg gag ctg cgg aag aag aag     968
Val Asp Lys Glu Arg Ala Glu Lys Asn Val Glu Leu Arg Lys Lys Lys
295                 300                 305                 310 cct gac tac ctg ccc tat gcc gag gac gag agc gtg gac gac ctg gcg    1016
Pro Asp Tyr Leu Pro Tyr Ala Glu Asp Glu Ser Val Asp Asp Leu Ala
                315                 320                 325 cag caa aaa cct cgc tct atc ctg tcc aag tat gac gaa gag ctt gaa    1064
Gln Gln Lys Pro Arg Ser Ile Leu Ser Lys Tyr Asp Glu Glu Leu Glu
        330                 335                 340 ggg gag cgg cca cat tcc ttc cgc ttg gag cag ggc ggc acg gct gat    1112
Gly Glu Arg Pro His Ser Phe Arg Leu Glu Gln Gly Gly Thr Ala Asp
            345                 350                 355 ggc ctg cgg gag cgg gag ctg gag gag atc cgg gcc aag ctg cgg ctg    1160
Gly Leu Arg Glu Arg Glu Leu Glu Glu Ile Arg Ala Lys Leu Arg Leu
    360                 365                 370 cag gct cag tcc ctg agc aca gtg ggg ccc cgg ctg gcc tcc gaa tac    1208
Gln Ala Gln Ser Leu Ser Thr Val Gly Pro Arg Leu Ala Ser Glu Tyr
375                 380                 385                 390 ctc acg cct gag gag atg gtg acc ttt aaa aag acc aag cgg agg gtg    1256
Leu Thr Pro Glu Glu Met Val Thr Phe Lys Lys Thr Lys Arg Arg Val
                395                 400                 405 aag aaa atc cgc aag aag gag aag gag gta gta gtg cgg gca gat gac    1304
Lys Lys Ile Arg Lys Lys Glu Lys Glu Val Val Val Arg Ala Asp Asp
        410                 415                 420 ttg ctg cct ctc ggg gac cag act cag gat ggg gac ttt ggt tcc aga    1352
Leu Leu Pro Leu Gly Asp Gln Thr Gln Asp Gly Asp Phe Gly Ser Arg
            425                 430                 435 ctg cgg gga cgg ggt cgc cgc cga gtg tcc gaa gtg gag gag gag aag    1400
Leu Arg Gly Arg Gly Arg Arg Val Ser Glu Val Glu Glu Glu Lys
    440                 445                 450 gag cct gtg cct cag ccc ctg ccg tcg gac gac acc cga gtg gag aac    1448
Glu Pro Val Pro Gln Pro Leu Pro Ser Asp Asp Thr Arg Val Glu Asn
455                 460                 465                 470 atg gac atc agt gat gag gag gaa ggt gga gct cca ccg ccg ggg tcc    1496
Met Asp Ile Ser Asp Glu Glu Glu Gly Gly Ala Pro Pro Pro Gly Ser
                475                 480                 485 ccg cag gtg ctg gag gag gac gag gcg gag ctg gag ctg cag aag cag    1544
Pro Gln Val Leu Glu Glu Asp Glu Ala Glu Leu Glu Leu Gln Lys Gln
        490                 495                 500 ctg gag aag gga cgc cgg ctg cga cag tta cag cag cta cag cag ctg    1592
Leu Glu Lys Gly Arg Arg Leu Arg Gln Leu Gln Gln Leu Gln Gln Leu
```

```
                505                 510                 515
cga gac agt ggc gag aag gtg gtg gag att gtg aag aag ctg gag tct    1640
Arg Asp Ser Gly Glu Lys Val Val Glu Ile Val Lys Lys Leu Glu Ser
    520                 525                 530 cgc cag cgg ggc tgg gag gag gat gag gat ccc gag cgg aag ggg gcc    1688
Arg Gln Arg Gly Trp Glu Glu Asp Glu Asp Pro Glu Arg Lys Gly Ala
535                 540                 545                 550 atc gtg ttc aac gcc acg tcc gag ttc tgc cgc acc ttg ggg gag atc    1736
Ile Val Phe Asn Ala Thr Ser Glu Phe Cys Arg Thr Leu Gly Glu Ile
                555                 560                 565 ccc acc tac ggg ctg gct ggc aat cgc gag gag cag gag gag ctc atg    1784
Pro Thr Tyr Gly Leu Ala Gly Asn Arg Glu Glu Gln Glu Glu Leu Met
            570                 575                 580 gac ttt gaa cgg gat gag gag cgc tca gcc aac ggt ggc tcc gaa tct    1832
Asp Phe Glu Arg Asp Glu Glu Arg Ser Ala Asn Gly Gly Ser Glu Ser
        585                 590                 595 gac ggg gag gag aac atc ggc tgg agc acg gtg aac ctg gac gag gag    1880
Asp Gly Glu Glu Asn Ile Gly Trp Ser Thr Val Asn Leu Asp Glu Glu
    600                 605                 610 aag cag cag cag gat ttc tct gct tcc tcc acc acc atc ctg gac gag    1928
Lys Gln Gln Gln Asp Phe Ser Ala Ser Ser Thr Thr Ile Leu Asp Glu
615                 620                 625                 630 gaa ccg atc gtg aat agg ggg ctg gca gct gcc ctg ctc ctg tgt cag    1976
Glu Pro Ile Val Asn Arg Gly Leu Ala Ala Ala Leu Leu Leu Cys Gln
                635                 640                 645 aac aaa ggg ctg ctg gag acc aca gtg cag aag gtg gcc cgg gtg aag    2024
Asn Lys Gly Leu Leu Glu Thr Thr Val Gln Lys Val Ala Arg Val Lys
            650                 655                 660 gcc ccc aac aag tcg ctg ccc tca gcc gtg tac tgc atc gag gat aag    2072
Ala Pro Asn Lys Ser Leu Pro Ser Ala Val Tyr Cys Ile Glu Asp Lys
        665                 670                 675 atg gcc atc gat gac aag tac agc cgg agg gag gaa tac cga ggc ttc    2120
Met Ala Ile Asp Asp Lys Tyr Ser Arg Arg Glu Glu Tyr Arg Gly Phe
    680                 685                 690 aca cag gac ttc aag gag aag gac ggc tac aaa ccc gac gtt aag atc    2168
Thr Gln Asp Phe Lys Glu Lys Asp Gly Tyr Lys Pro Asp Val Lys Ile
695                 700                 705                 710 gaa tac gtg gat gag acg ggc cgg aaa ctc aca ccc aag gag gct ttc    2216
Glu Tyr Val Asp Glu Thr Gly Arg Lys Leu Thr Pro Lys Glu Ala Phe
                715                 720                 725 cgg cag ctg tcg cac cgc ttc cat ggc aag ggc tca ggc aag atg aag    2264
Arg Gln Leu Ser His Arg Phe His Gly Lys Gly Ser Gly Lys Met Lys
            730                 735                 740 aca gag cgg cgg atg aag aag ctg gac gag gag gcg ctc ctg aag aag    2312
Thr Glu Arg Arg Met Lys Lys Leu Asp Glu Glu Ala Leu Leu Lys Lys
        745                 750                 755 atg agc tcc agc gac acg ccc ctg ggc acc gtg gcc ctg ctc cag gag    2360
Met Ser Ser Ser Asp Thr Pro Leu Gly Thr Val Ala Leu Leu Gln Glu
    760                 765                 770 aag cag aag gct cag aag acc ccc tac atc gtg ctc agc ggc agc ggc    2408
Lys Gln Lys Ala Gln Lys Thr Pro Tyr Ile Val Leu Ser Gly Ser Gly
775                 780                 785                 790 aag agc atg aac gcg aac acc atc acc aag tgacagcgcc ctcccgtagt      2458
Lys Ser Met Asn Ala Asn Thr Ile Thr Lys
                795                 800 cggccctgcc tcaaccttca tattaaataa agctccctcc ttatttttaa aaaaaaaaa   2518 aaaaaaaaa                                                          2527
```

-continued

<210> SEQ ID NO 2
<211> LENGTH: 800
<212> TYPE: PRT
<213> ORGANISM: Homo sapiens

<400> SEQUENCE: 2

Met Gly Ser Ser Lys Lys His Arg Gly Glu Lys Glu Ala Ala Gly Thr
1               5                   10                  15

Thr Ala Ala Gly Thr Gly Gly Ala Thr Glu Gln Pro Pro Arg His
            20                  25                  30

Arg Glu His Lys Lys His Lys His Arg Ser Gly Gly Ser Gly Gly Ser
        35                  40                  45

Gly Gly Glu Arg Arg Lys Arg Ser Arg Glu Arg Gly Gly Glu Arg Gly
    50                  55                  60

Ser Gly Arg Arg Gly Ala Glu Ala Glu Ala Arg Ser Ser Thr His Gly
65                  70                  75                  80

Arg Glu Arg Ser Gln Ala Glu Pro Ser Glu Arg Val Lys Arg Glu
            85                  90                  95

Lys Arg Asp Asp Gly Tyr Glu Ala Ala Ala Ser Ser Lys Thr Ser Ser
            100                 105                 110

Gly Asp Ala Ser Ser Leu Ser Ile Glu Glu Thr Asn Lys Leu Arg Ala
        115                 120                 125

Lys Leu Gly Leu Lys Pro Leu Glu Val Asn Ala Ile Lys Lys Glu Ala
    130                 135                 140

Gly Thr Lys Glu Glu Pro Val Thr Ala Asp Val Ile Asn Pro Met Ala
145                 150                 155                 160

Leu Arg Gln Arg Glu Glu Leu Arg Glu Lys Leu Ala Ala Lys Glu
            165                 170                 175

Lys Arg Leu Leu Asn Gln Lys Leu Gly Lys Ile Lys Thr Leu Gly Glu
            180                 185                 190

Asp Asp Pro Trp Leu Asp Asp Thr Ala Ala Trp Ile Glu Arg Ser Arg
        195                 200                 205

Gln Leu Gln Lys Glu Lys Asp Leu Ala Glu Lys Arg Ala Lys Leu Leu
    210                 215                 220

Glu Glu Met Asp Gln Glu Phe Gly Val Ser Thr Leu Val Glu Glu Glu
225                 230                 235                 240

Phe Gly Gln Arg Arg Gln Asp Leu Tyr Ser Ala Arg Asp Leu Gln Gly
            245                 250                 255

Leu Thr Val Glu His Ala Ile Asp Ser Phe Arg Glu Gly Glu Thr Met
            260                 265                 270

Ile Leu Thr Leu Lys Asp Lys Gly Val Leu Gln Glu Glu Asp Val
        275                 280                 285

Leu Val Asn Val Asn Leu Val Asp Lys Glu Arg Ala Glu Lys Asn Val
    290                 295                 300

Glu Leu Arg Lys Lys Pro Asp Tyr Leu Pro Tyr Ala Glu Asp Glu
305                 310                 315                 320

Ser Val Asp Asp Leu Ala Gln Gln Lys Pro Arg Ser Ile Leu Ser Lys
            325                 330                 335

Tyr Asp Glu Glu Leu Glu Gly Glu Arg Pro His Ser Phe Arg Leu Glu
            340                 345                 350

Gln Gly Gly Thr Ala Asp Gly Leu Arg Glu Arg Glu Leu Glu Glu Ile
        355                 360                 365

Arg Ala Lys Leu Arg Leu Gln Ala Gln Ser Leu Ser Thr Val Gly Pro
    370                 375                 380

-continued

```
Arg Leu Ala Ser Glu Tyr Leu Thr Pro Glu Glu Met Val Thr Phe Lys
385                 390                 395                 400

Lys Thr Lys Arg Arg Val Lys Lys Ile Arg Lys Glu Lys Glu Val
            405                 410                 415

Val Val Arg Ala Asp Asp Leu Leu Pro Leu Gly Asp Gln Thr Gln Asp
                420                 425                 430

Gly Asp Phe Gly Ser Arg Leu Arg Gly Arg Gly Arg Arg Val Ser
        435                 440                 445

Glu Val Glu Glu Glu Lys Glu Pro Val Pro Gln Pro Leu Pro Ser Asp
    450                 455                 460

Asp Thr Arg Val Glu Asn Met Asp Ile Ser Asp Glu Glu Glu Gly Gly
465                 470                 475                 480

Ala Pro Pro Pro Gly Ser Pro Gln Val Leu Glu Glu Asp Glu Ala Glu
                485                 490                 495

Leu Glu Leu Gln Lys Gln Leu Glu Lys Gly Arg Arg Leu Arg Gln Leu
            500                 505                 510

Gln Gln Leu Gln Gln Leu Arg Asp Ser Gly Glu Lys Val Val Glu Ile
        515                 520                 525

Val Lys Lys Leu Glu Ser Arg Gln Arg Gly Trp Glu Glu Asp Glu Asp
    530                 535                 540

Pro Glu Arg Lys Gly Ala Ile Val Phe Asn Ala Thr Ser Glu Phe Cys
545                 550                 555                 560

Arg Thr Leu Gly Glu Ile Pro Thr Tyr Gly Leu Ala Gly Asn Arg Glu
                565                 570                 575

Glu Gln Glu Glu Leu Met Asp Phe Glu Arg Asp Glu Glu Arg Ser Ala
            580                 585                 590

Asn Gly Gly Ser Glu Ser Asp Gly Glu Glu Asn Ile Gly Trp Ser Thr
        595                 600                 605

Val Asn Leu Asp Glu Glu Lys Gln Gln Gln Asp Phe Ser Ala Ser Ser
    610                 615                 620

Thr Thr Ile Leu Asp Glu Glu Pro Ile Val Asn Arg Gly Leu Ala Ala
625                 630                 635                 640

Ala Leu Leu Leu Cys Gln Asn Lys Gly Leu Leu Glu Thr Thr Val Gln
                645                 650                 655

Lys Val Ala Arg Val Lys Ala Pro Asn Lys Ser Leu Pro Ser Ala Val
            660                 665                 670

Tyr Cys Ile Glu Asp Lys Met Ala Ile Asp Asp Lys Tyr Ser Arg Arg
        675                 680                 685

Glu Glu Tyr Arg Gly Phe Thr Gln Asp Phe Lys Glu Lys Asp Gly Tyr
    690                 695                 700

Lys Pro Asp Val Lys Ile Glu Tyr Val Asp Glu Thr Gly Arg Lys Leu
705                 710                 715                 720

Thr Pro Lys Glu Ala Phe Arg Gln Leu Ser His Arg Phe His Gly Lys
                725                 730                 735

Gly Ser Gly Lys Met Lys Thr Glu Arg Arg Met Lys Lys Leu Asp Glu
            740                 745                 750

Glu Ala Leu Leu Lys Lys Met Ser Ser Asp Thr Pro Leu Gly Thr
    755                 760                 765

Val Ala Leu Leu Gln Glu Lys Gln Lys Ala Gln Lys Thr Pro Tyr Ile
    770                 775                 780

Val Leu Ser Gly Ser Gly Lys Ser Met Asn Ala Asn Thr Ile Thr Lys
785                 790                 795                 800
```

TUMOR ANTIGEN PROTEINS, GENES THEREOF, AND TUMOR ANTIGEN PEPTIDES

This application is the national phase under 35 U.S.C. §371 of prior PCT International Application No. PCT/JP97/01893 which has an International filing date of Jun. 4, 1997 which designated the United States of America.

TECHNICAL FIELD

The present invention relates to medicines for activating antitumor immunity and for treating autoimmune diseases as well as to diagnosis of tumors or autoimmune diseases. In particular, the present invention relates to novel tumor antigen proteins, novel genes therefor, novel tumor antigen peptides, and the like.

PRIOR ART

It is known that the immune system, particularly T cells, plays an important role in vivo in tumor rejection. Indeed, infiltration of lymphocytes having cytotoxic effects on tumor cells has been observed in human tumor foci (*Arch. Surg.*, 126:200–205, 1990), and cytotoxic T lymphocytes (CTLs) recognizing autologous tumor cells have been isolated from melanomas without great difficulties (e.g., *Immunol. Today*, 8:385, 1987; *J. Immunol.*, 138:989, 1987; and *Int. J. Cancer*, 52:52–59, 1992). In addition, the results of clinical treatment of melanomas by T cell introduction also suggest the importance of T cells in tumor rejection (*J. Natl. Cancer Inst.*, 86:1159, 1994).

Although it has long been unknown about target molecules for CTLs attacking autologous tumor cells, the recent advance in immunology and molecular biology has gradually begun elucidating such target molecules. Specifically, it has been found that using T cell receptors (TCRs), CTL recognizes a complex consisting of tumor antigen peptide and major histocompatibility complex (MHC) class I antigen, and thereby attacks autologous tumor cells.

Tumor antigen peptides are generated from tumor antigen proteins. Thus, the proteins are intracellularly synthesized and then degraded in cytoplasm into the peptides by proteasome. On the other hand, MHC class I antigens formed at endoplasmic reticulum bind to the above tumor antigen peptides, and are transported via cis Golgi to trans Golgi, i.e., the mature side, and expressed on the cell surface (*Rinsho-Menneki*, 27(9):1034–1042, 1995).

As such a tumor antigen protein, T. Boon et al. identified a protein named MAGE from human melanoma cells for the first time in 1991 (*Science*, 254:1643–1647, 1991), and thereafter several additional tumor antigen proteins have been identified from melanoma cells.

As described in the review by T. Boon et al. (*J. Exp. Med.*, 183, 725–729, 1996), tumor antigen proteins hitherto identified can be divided into the following four categories.

Tumor antigen proteins belonging to the first category are those proteins which are expressed only in testis among normal tissues, while they are expressed in melanoma, head and neck cancer, non-small cell lung cancer, bladder cancer and others, among tumor tissues. Among tumor antigen proteins in this category are the above-described MAGE and analogous proteins constituting a family of more than 12 members (*J. Exp. Med.*, 178:489–495, 1993), as well as BAGE (*Immunity*, 2:167–175, 1995) and GAGE (*J. Exp. Med.*, 182:689–698, 1995), all of which have been identified from melanoma cells.

Although some of such tumor antigen proteins in this category are highly expressed in melanoma, their expression is observed in only 10 to 30% of patients having a particular tumor other than melanoma, and therefore, they can not be applied widely to treatments or diagnoses of various tumors.

Tumor antigen proteins belonging to the second category are those proteins which are expressed only in melanocytes and retina among normal tissues, while the expression is observed only in melanomas among tumor tissues. Since these tissue-specific proteins are highly expressed in melanomas, they function as tumor antigen proteins specific for melanomas. Among tumor antigen proteins in this category are tyrosinase (*J. Exp. Med.*, 178:489–495, 1993), MART-1 (*Proc. Natl. Acad. Sci. USA*, 91:3515, 1994), gp100 (*J. Exp. Med.*, 179:1005–1009, 1994), and gp75 (*J. Exp. Med.*, 181:799–804, 1995), genes for which have all been cloned from melanoma cells. Additionally and separately identified Melan-A (*J. Exp. Med.*, 180:35, 1994) has proved to be the same molecule as MART-1.

However, the tumor antigen proteins in this category can not be used widely for treatments or diagnoses of various tumors, since they are not expressed in tumors other than melanoma.

Tumor antigen proteins belonging to the third category are those proteins which yield, through tumor-specific mutations, tumor antigen peptides newly recognized by CTL. Among tumor antigen proteins in this category are mutated CDK4 (*Science*, 269:1281–1284, 1995), β-catenin (*J. Exp. Med.*, 183:1185–1192, 1996), and MUM-1 (*Proc. Natl. Acad. Sci. USA*, 92:7976–7980, 1995). In CDK4 and β-catenin, a single amino acid mutation increases the binding affinity of the peptides to MHC class I antigen, and allows them to be recognized by T cells. In MUM-1, its intron normally untranslated is translated due to mutation, and the peptide thus generated is recognized by T cells. However, since such mutations occur at low frequency, they can not be applied widely to treatments or diagnoses of various tumors.

As a tumor antigen protein belonging to the fourth category, P15 has been identified from melanoma cells, which is a protein widely expressed in normal tissues and which is also recognized by CTL (*J. Immunol.* 154:5944–5955, 1995).

Tumor antigen proteins or peptides hitherto known have been identified as follows.

In such identification, a set of tumor cells and CTLs attacking the tumor cells (usually established from lymphocytes of the same patient from whom the tumor cells are obtained) are firstly provided. Then, the cells from this set are used to directly identify tumor antigen peptides, or used to determine the gene encoding the tumor antigen protein from which corresponding tumor antigen peptides are identified.

Specifically, in the case where tumor antigen peptides are directly identified, tumor antigen peptides bound to MHC class I antigens in tumor cells are extracted under acidic conditions, and separated into various peptides using high-performance liquid chromatography. Cells expressing MHC class I antigen, but not expressing tumor antigen protein (for example, B cells from the same patient), are then pulsed with such various peptides, and examined for their reactivity with CTL to identify tumor antigen peptides. Then, the sequences of the peptides thus identified are further determined by, for example, mass spectrometry. In this way, tumor antigen peptides derived from Pmel 17 which is the same molecule as gp100 have been identified from melanoma cells (*Science*, 264:716–719, 1994).

In order to firstly determine the gene encoding tumor antigen protein and then to identify therefrom corresponding tumor antigen peptides, the gene encoding tumor antigen protein may be cloned using molecular biological techniques. cDNAs are prepared from tumor cells, and cotransfected with MHC class I antigen gene into cells not expressing tumor antigen proteins (for example, COS cells), in order to express them transiently. The products thus expressed are then repeatedly screened on the basis of their reactivity with CTL, until the gene encoding tumor antigen protein may finally be isolated. In this way, the genes for the above-mentioned MAGE, tyrosinase, MART-1, gp100, and gp75 have been cloned.

In order to deduce and identify the presented tumor antigen peptides actually bound to MHC class I antigens on the basis of the information about such tumor antigen gene, the methods as described below are used. Firstly, fragments of the gene encoding tumor antigen protein, having various sizes, are prepared using, for example, PCR, exonucleases, or restriction enzymes, and cotransfected with MHC class I antigen gene into cells not expressing tumor antigen proteins (e.g., COS cells), in order to express them transiently. The region(s) which include tumor antigen peptides are then identified on the basis of their reactivity with CTL. Subsequently, peptides are synthesized. Cells expressing MHC class I antigen but not expressing tumor antigen proteins are then pulsed with the synthesized peptides, and examined for their reactions with CTL to identify the tumor antigen peptides (*J. Exp. Med.*, 176:1453, 1992; *J. Exp. Med.*, 179:24, 759, 1994). The sequence regularities (motifs) for peptides, which are bound and presented by certain types of MHC such as HLA-A1, -A0201, -A0205, -A11, -A31, -A6801, -B7, -B8, -B2705, -B37, -Cw0401, and -Cw0602 have been known (*Immunogenetics*, 41:178–228, 1995), and therefore, candidates for tumor antigen peptides may also be designed by making reference to such motifs, and such candidate peptides may be practically synthesized and examined in the same way as described above (*Eur. J. Immunol.*, 24:759, 1994; *J. Exp. Med.*, 180:347, 1994).

Furthermore, it is another possibility that tumor antigen proteins expressed at high level in tumors are expressed also in normal tissues, and cause autoimmune diseases by inducing excessive immune response against such tumor antigen proteins. For example, it was reported that when a combination of a chemotherapeutic agent and IL-2 was used for treating melanomas, appearance of leukoderma was observed (*J. Clin. Oncol.*, 10:1338–1343, 1992). This is probably because CTLs or antibodies against the complexes consisting of fragments of the tumor antigen protein expressed in melanomas (referred to as peptide fragments) and MHC class I antigens were inductively produced, and they affected normal skin tissues to develop leukoderma, an autoimmune disease-like symptom.

SUBJECT THAT THE INVENTION IS TO SOLVE

As described above, some of the known tumor antigen proteins are expressed only in limited tumors, and others are expressed only in a small number of patients having a particular tumor even if they are expressed in various kinds of tumor, and therefore, they can not be used widely for treatments or diagnoses of various tumors.

Thus, the present invention aims to provide tumor antigen proteins or fragments thereof (hereinafter referred to as "peptide fragments" or as "tumor antigen peptides") which, unlike the known tumor antigen proteins or their peptide fragments, can be used for treatments or diagnoses of a wide variety of tumors including squamous cell carcinoma, or which can be applied to major part of patients having a particular tumor even if they can be used only for limited tumors, or which can be applied to various tumors as a therapeutic or diagnostic assistant in the treatment or diagnosis for such tumors.

Squamous cell carcinoma is one of the most common cancers in human. In particular, squamous cell carcinomas in esophageal cancer and lung cancer are known to be relatively resistant to current chemotherapy and radiotherapy. Also in this regard, it is desired to develop specific immunotherapies such as those which use tumor antigen proteins or corresponding tumor antigen peptides.

Furthermore, when one develops autoimmune disease due to excessively induced specific immunity raised by tumor antigen protein, it would be desirous treatments to specifically block such immune response using, for example, antisense DNA/RNA for the gene encoding tumor antigen proteins or antagonists for the tumor antigen peptides.

MEANS FOR SOLVING THE SUBJECT

With the aim of obtaining tumor antigen protein or corresponding tumor antigen peptides which can be applied widely to treatments or diagnoses of various tumors including, in particular, squamous cell carcinoma, the present inventors tried to identify tumor antigen proteins from tumors other than melanoma.

Specifically, the present inventors established a squamous cell carcinoma cell line KE-4 derived from esophageal cancer (hereinafter referred to as esophageal cancer cell line KE-4 or simply as KE-4), and also established CTL (hereinafter referred to as KE-4CTL) which recognizes tumor antigen peptides restricted to HLA-A2601 which is a MHC class I antigen expressed in said KE-4 (*Cancer Res.*, 55:4248–4253, 1995).

Fibroblast cell line VA-13 was then cotransfected with a recombinant plasmid of cDNA library prepared from KE-4 and a recombinant plasmid containing HLA-A2601 cDNA. The resulting transfectants were treated with KE-4CTL, and screened by measuring the amount of produced IFN-γ to determine whether KE-4-CTL was activated. As a result, the inventors succeeded in cloning a novel gene encoding tumor antigen protein of the present invention for the first time from tumor cells other than melanoma.

Thus, the gist of the present invention relates to:

(1) DNA encoding a protein having the amino acid sequence shown in SEQ ID NO: 2(Identification Method: P) or a variant protein thereof in which one or more amino acid residues are substituted, deleted or added, said protein and variant protein thereof being capable of yielding, through its intracellular decomposition, peptide fragments which can bind to MHC class I antigen and which can be recognized by T cells in such binding state;

(2) DNA which comprises the base sequence shown in SEQ ID NO: 1(Identification Method E), or a variant DNA which hybridizes to said DNA under stringent conditions, the protein produced by expression of said DNA and variant DNA being capable of yielding, through its intracellular decomposition, peptide fragments which can bind to MHC class I antigen and which can be recognized by T cells in such binding state;

(3) medicines comprising DNA of the above item (1) or (2) as an active ingredient;

(4) expression plasmids comprising DNA of the above item (1) or (2);

(5) transformants transformed with the expression plasmid of the above item (4);
(6) tumor antigen proteins produced by expression of DNA of the above item (1) or (2);
(7) tumor antigen peptides comprising part of the protein of the above item (6) which can bind to MHC class I antigen to be recognized by T cells, or derivatives thereof having functionally equivalent properties;
(8) tumor antigen peptides of the above item (7) which comprise all or part of the amino acid sequence of positions 749–757, 736–744, 785–793, or 690–698 in the amino acid sequence of SEQ ID NO: 2, or derivatives thereof having functionally equivalent properties;
(9) medicines comprising, as an active ingredient, tumor antigen protein of the above item (6), tumor antigen peptide or derivative thereof defined in the above item (7) or (8). (10) antibodies which specifically bind to the tumor antigen proteins of the above item (6) or tumor antigen peptides of the above item (7) or (8); and (11) DNA comprising 8 or more bases having a sequence complementary to the coding or 5' non-coding sequence of DNA having the base sequence shown in SEQ ID NO: 2 or RNA corresponding to said DNA, or chemically modified variant thereof.

MODE FOR CARRYING OUT THE INVENTION

DNAs of the present invention encode a novel tumor antigen protein, and may include a DNA which encodes a protein having the amino acid sequence shown in SEQ ID NO: 2 or a variant protein thereof in which one or more amino acid residues are substituted, deleted or added, said protein and variant protein being capable of yielding, through its intracellular decomposition, peptide fragments which can bind to MHC class I antigen and which can be recognized by T cells in such binding state, as well as DNA which comprises the base sequence shown in SEQ ID NO: 1 or variant DNA thereof which hybridizes to said DNA under stringent conditions, the protein produced by expression of said DNA and variant DNA being capable of yielding, through its intracellular decomposition, peptide fragments which can bind to MHC class I antigen and which can be recognized by T cells in such binding state.

As used herein, the phrase "variant protein thereof in which one or more amino acid residues are substituted, deleted, or added" refers to so-called variant proteins artificially prepared, to naturally-occurring polymorphism, or to proteins produced by mutation or modification but having functionally equivalent properties. DNAs encoding such variant proteins may be prepared using, for example, the methods described in Sambrook, J. et al., *Molecular Cloning: A Laboratory Manual,* 2nd ed., vols. 1∫3 (Cold Spring Harbor Laboratory Press, New York, 1989), such as site-directed mutagenesis or PCR method. In this context, the number of amino acid residues to be substituted, deleted, or added should be such a number that permits the substitution, deletion or addition by well-known methods such as site-directed mutagenesis described above.

"Variant DNA which hybridizes to DNA under stringent conditions" as described herein may be obtained using, for example, the methods described in Molecular Cloning mentioned above. In this context, "stringent conditions" refers to, for example, such conditions that hybridization is conducted at 42° C. in a solution containing 6×SSC (20 ×SSC means 333 mM sodium citrate and 333 mM NaCl), 0.5% SDS, and 50% formamide, followed by washing in a solution of 0.1 ×SSC and 0.5% SDS at 68° C., or those conditions described in Nakayama el al., *Bio-Jikken-Illustrated,* vol. 2, "Idenshi-Kaiseki-no-Kiso (Basis for Gene Analysis)", pp. 148–151, Shujunsha,.1995. For the purpose of this invention, the protein produced by expression of such hybridizable DNA should comprise a peptide segment which is capable of binding to MHC class I antigen and recognized by T cells.

As used herein, "protein and variant protein which are capable of yielding, through its intracellular decomposition, peptide fragments which can bind to MHC class I antigen and which can be recognized by T cells in such binding state" (hereinafter, such protein is sometimes referred to as tumor antigen protein) means that partial peptide consisting of part of the amino acid sequence of such protein or variant protein can bind to MHC class I antigen, and that when bound to MHC class I antigen and presented on cell surface, the complex of the peptide fragment and MHC class I antigen can be recognized by T cells capable of specifically binding thereto, and transduces signals to T cells. In this context, such binding means non-covalent binding.

In order to confirm that a given peptide fragment is capable of binding to MHC class I antigen and recognized by T cells, the peptide fragment may be bound to MHC class I antigen and presented on cell surface by expressing it endogenously in an appropriate cell or by adding it exogenously to an appropriate cell (pulsing). The peptide presenting cells may be then treated with T cells specific to the tumor antigen protein, and cytokines produced by the T cells may be measured. Alternatively, as a method measuring the cytotoxic activity of T cells against the peptide-presenting cells, a method using the peptidepresenting cells labeled with $^{51}$Cr (*Int. J. Cancer,* 58:317 (1994)) may also be used. In such methods, CTLs are preferably used as the T cells recognizing the peptide.

DNA of the present invention may be used as an active ingredient of medicines. For example, medicines which comprise DNA of the present invention as an active ingredient can be used for treating or preventing tumors by administering the DNA of the present invention to tumor patients. When DNA of the present invention is administered, the tumor antigen protein is expressed at high level in the cells. As a result, the tumor antigen peptides bind to MHC class I antigen and presented on the cell surface at high density. This will cause efficient proliferation of tumor-specific CTLs in the body, allowing treatment or prevention of the tumor. Administration and introduction of DNA of the present invention into cells may be achieved using viral vectors or according to any one of other procedures (*Nikkei-Science, April,* 1994, pp. 20–45; *Gekkan-Yakuji,* 36(1), 23–48 (1994); *Jikken-Igaku-Zokan,* 12(15), 1994, and references cited therein).

Examples of the methods using viral vectors include those methods in which DNA of the present invention is incorporated into DNA or RNA virus such as retrovirus, adenovirus, adeno-associated virus, herpesvirus, vaccinia virus, poxvirus, poliovirus, or Sindbis virus, and introduced into cells. Among them, the methods using retrovirus, adenovirus, adeno-associated virus, or vaccinia virus are particularly preferred.

Other methods may include those in which expression plasmids are directly injected intramuscularly (DNA vaccination), the liposome method, Lipofectin method, microinjection, the calcium phosphate method, and electroporation, with DNA vaccination and the liposome method being particularly preferred.

In order to make DNA of the present invention act as medicine in practice, one can use either of two methods: in vivo method in which DNA is directly introduced into the body, or ex vivo method in which certain cells are removed from human, and after introducing DNA into said cells extracorporeally, reintroduced into the body (*Nikkei-Science,* April, 1994, pp. 20–45; *Gekkan-Yakuji,* 36(1), 23–48 (1994); *Jikkenn-Igaku-Zokan,* 12(15), 1994; and references cited therein). In vivo method is rather preferred.

In the case of in vivo methods, DNA may be administered by any appropriate route depending on the diseases and symptoms to be treated, and other factors. For example, it may be administered by intravenous, intraarterial, subcutaneous, intracutaneous, or intramuscular routes. In the case of in vivo methods, such medicines may be administered in various dosage forms such as solution, and they are typically formulated into injections containing DNA of the present invention as an active ingredient, which may also include, if necessary, conventional carriers. When DNA of the present invention is included in liposomes or membrane-fused liposomes (such as Sendai virus (HVJ)-liposomes), such medicines may be in the form of suspension, frozen drug, centrifugally-concentrated frozen drug or the like.

Although the amount of DNA of the present invention in such formulations may vary depending on, for example, the disease to be treated, the age and body weight of a particular patient, it is usually preferred to administer 0.0001–100 mg, more preferably 0.001–10 mg, of DNA of the present invention every several days to every several months.

Furthermore, the tumor antigen protein can be prepared in large quantities by recombinant DNA techniques using DNA of the present invention.

Preparation of tumor antigen protein by expression of DNA of the present invention may be achieved according to many publications and references such as Molecular Cloning mentioned above. An expression plasmid which can replicate and function in host cells is constructed by adding regulatory gene(s) such as a promoter which contrrolls transcription (e.g., trp, lac, T7, or SV40 early promoter) upstream to the DNA to be expressed and by inserting the resultant DNA into an appropriate vector (e.g., pSV-SPORT1). The expression plasmid is then introduced into appropriate host cells to obtain transformants. Examples of host cell include, for example, prokaryotes such as *Escherichia coli*, unicellular eukaryotes such as yeast, and cells derived from multicellular eukaryotes such as insects or animals. Gene transfer into host cells may be achieved by, for example, the calcium phosphate method, DEAE-dextran method, or the electric pulse method. Transformants cultured in appropriate medium produce the protein of interest. The tumor antigen protein thus obtained may be isolated and purified according to standard biochemical procedures.

In the present invention, "peptide fragments which can bind to MHC class I antigen and which can be recognized by T cells in such binding state", which may be produced through intracellular decomposition of tumor antigen protein of the present invention, i.e., "tumor antigen peptides", may be determined as follows.

Firstly, fragments of DNA encoding tumor antigen protein and having various sizes are prepared using, for example, PCR, exonucleases, or restriction enzymes, and then inserted into expression vectors as described above. The vectors are then cotransfected into cells not expressing tumor antigen proteins (e.g., COS cells), with a plasmid which comprises a gene for MHC class I antigen that presents tumor antigens, in order to express them transiently. The regions which include the tumor antigen peptides are identified on the basis of the reactivity of the transfectants with CTL. Subsequently, various peptides included in such regions are synthesized. Cells expressing MHC class I antigen which presents tumor antigens but not expressing tumor antigen proteins are pulsed with the synthesized peptides, and examined for their reaction with CTL to identify the tumor antigen peptides (*J. Exp. Med.,* 176:1453, 1992; *J. Exp. Med.,* 179:24, 759, 1994).

Alternatively, the sequence regularities (motifs) of antigen peptides bound and presented by certain MHC types such as HLA-A1, A0201, -A0205, -A11, -A24, -A31, -A6801, -B7, -B8, -B2705, -B37, -Cw0401, and -Cw0602 have been known, and threfore, candidates for tumor antigen peptides may also be selected making reference to such motifs, and such candidate peptides may be synthesized and identified in the manner as described above (*Eur. J. Immunol.,* 24:759, 1994; *J. Exp. Med.,* 180:347, 1994).

It is also known that MHC includes class II antigens besides class I antigens, and that conjugates of such MHC class II antigen with particular tumor antigen peptides, which may be produced from tumor antigen protein through phagocytosis and decomposition by antigen-presenting cells, such as macrophage, will activate tumor-specific helper T cells (*J. Immunol.,* 146:1708–1714, 1991).

The successful cloning of the novel tumor antigen protein gene of the present invention also enables those skilled in the art to determine additional tumor antigen peptides which bind to MHC class II antigen described above. Specifically, such antigen peptides may be determined on the basis of their reactivity with T cells or based on known information on motifs of such antigen peptides, in the same manner as MHC class I antigen.

The tumor antigen peptides thus determined may be prepared by usual methods known in peptide chemistry such as those described in "*Peptide Synthesis*" (Interscience, New York, 1966), "*The Proteins*" (vol. 2, Academic Press Inc., New York, 1976), "*Pepuchido-Gosei*" (Maruzen, 1975), or "*Pepuchido-Gosei-no-Kiso-to-Jikkenn*" (Maruzen, 1985). In particular, such peptide can be synthesized by selecting either the liquid phase method or the solid phase method depending on the structure of its C-terminus, with the liquid phase method being more preferable. Thus, peptides may be prepared by protecting and deprotecting functional groups in amino acids, and elongating them by a single residue or several residues. Protecting groups for functional groups on amino acids are described, for example, in the abovementioned publications concerning peptide chemistry.

For the purpose of the present invention, "tumor antigen peptides" may be defined as peptide fragments derived from either a protein having the amino acid sequence shown in SEQ ID NO: 2 or a variant protein thereof as defined above. Although the following description mainly relates to tumor antigen peptides derived from the protein having the amino acid sequence shown in SEQ ID NO: 2 as well as derivatives thereof, it will be understood that such description can apply to tumor antigen peptides derived from variant proteins.

Tumor antigen peptides produced by intracellular decomposition of the protein shown in SEQ ID NO: 2 are not specifically restricted, and may include, but not limited to, those peptides that comprise all or part of the amino acid sequence of positions 749–757, 736–744, 785–793, or 690–698 in the amino acid sequence shown in SEQ ID NO: 2. Preferred are those peptides that consist of 9 amino acid residues, and those peptides that consists of the amino acid sequence of positions 749–757, 736–744, 785–793, or 690–698 in SEQ ID NO: 2 are particularly preferred.

Regarding tumor antigen peptides described herein, for example, the peptide consisting of the amino acid sequence of positions 749–757 in SEQ ID NO: 2 is sometimes abbreviated as "749–757".

As used herein, "derivatives of tumor antigen peptide" refers to those derivatives which have properties functionally equivalent to such tumor antigen peptide and in which some of the amino acid residues in said peptide are substituted, deleted, or added, or to those derivatives in which amino group(s) or carboxy group(s) in said peptide(s) or derivatives described just above are modified. In particular, examples of such derivatives may include those derivatives in which, in a tumor antigen peptide of the present invention comprising all or part of the amino acid sequence of positions 749–757, 736–744, 785–793, or 690–698 in the amino acid sequence of SEQ ID NO: 2, some of the amino acid residues in the amino acid sequence of positions 749–757, 736–744, 785–793, or 690–698 are substituted or deleted, or other amino acid residue(s) are added thereto.

Among derivatives in which some of the amino acid residues in said peptide are substituted, deleted, or added, preferred are those derivatives which retain the epitope regions in the tumor antigen peptides involved in their binding with CTL and in which amino acid residue(s) in the tumor antigen peptides involved in their binding with MHC class I antigen are substituted, deleted, or added. Among such derivatives, those derivatives in which a single amino acid residue is substituted are more preferred (*Immunol.* 84:298–303, 1995). For antigen peptides derived from melanoma tumor antigen protein gp 100, it is reported that substitution of amino acid(s) in the binding site for MHC class I antigen has resulted in its stronger binding with MHC class I antigen, and also caused stronger induction of CTL specific to such antigen peptide when used in in vitro stimulation of peripheral blood lymphocytes derived from melanoma patients (*J. Immunol.*, 157:2539–2548, 1996).

Such derivatives can be easily synthesized using a commercially available peptide synthesizer, and the binding affinity of synthesized derivatives to MHC class I antigen may be easily measured by competitive inhibition assay between said derivatives and radiolabeled standard peptide for binding to MHC class I antigen (R. T. Kubo et al., *J. Immunol.*, 152:3913, 1994). Thus, by subjecting various peptide derivatives to such assay, peptide derivatives having CTL-inducing activity can be easily selected. Since the peptide derivatives thus selected can bind to MHC class I antigen more strongly while retaining their binding ability to CTL, they can be used as more efficient tumor antigen peptides.

Examples of modifying group for amino group may include acyl groups, and in particular, alkanoyl groups of 1–6 carbon atoms, alkanoyl groups of 1–6 carbon atoms substituted by phenyl group, carbonyl groups substituted by cycloalkyl group of 5–7 carbon atoms, alkylsulfonyl groups of 1–6 carbon atoms, phenylsulfonyl groups, and the like.

Modifying group for carboxy group include, for example, ester and amide groups. Specific examples of such ester group may be alkyl ester groups of 1–6 carbon atoms, alkyl ester groups of 0–6 carbon atoms substituted by phenyl group, and cycloalkyl ester groups of 5–7 carbon atoms, and specific examples of such amide group may be an amide group, amide groups substituted by one or two alkyl groups of 1–6 carbon atoms, amide groups of 0–6 carbon atoms substituted by one or two alkyl groups substituted by phenyl, and amide groups forming a 5–7 membered azacycloalkane including the amide nitrogen as a ring member. "Antibodies" of the present invention may be easily prepared according to, for example, the methods described in Lane, H.D. et al., *Antibodies: A Laboratory Manual* (Cold Spring Harbor Labortory Press, New York, 1989). Specifically, antibodies which recognize tumor antigen proteins or tumor antigen peptides, and antibodies which further neutralize their activities may be easily prepared by immunizing an animal with such tumor antigen protein or tumor antigen peptide using conventional procedures. Such antibodies may be used in, for example, affinity chromatography, screening of cDNA library, immunological diagnosis, or preparation of medicines. Such immunological diagnosis may include immunoblotting, radioimmunoassay (RIA), enzyme-linked immunosorbent assay (ELISA), fluorescent or luminescent assay, and the like.

As used herein, "DNA comprising 8 or more bases having a sequence complementary to the coding sequence or 5' non-coding sequence of DNA comprising the base sequence shown in SEQ ID NO: 1 or RNA corresponding to said DNA" means an antisense strand of double stranded DNA, or RNA corresponding to such antisense strand DNA, comprising 8 or more bases (hereinafter referred to as antisense oligonucleotides).

For example, as such antisense oligonucleotides, DNA may be prepared on the basis of the base sequence of the gene encoding tumor antigen protein of the present invention, and corresponding RNA may be prepared by incorporating such DNA into an expression plasmid in the antisense direction.

Although such antisense oligonucleotides may have a sequence complimentary to any part of the coding sequence or 5' non-coding sequence of DNA of the present invention comprising the base sequence shown in SEQ ID NO: 1, they preferably have a sequence complimentary to transcription initiation site, translation initiation site, 5' non-translated region, a boundary region between exon and intron, or 5' CAP region.

In the above description, "chemically modified variants" of "DNA or RNA corresponding to said DNA" (hereinafter referred to as chemically modified variant of antisense oligonucleotides) may include those variants which have increased transferability into cells or increased stability in cells. Specific examples of the variants include phosphorothioate, phosphorodithioate, alkyl phosphotriester, alkyl phosphonate, or alkyl phosphoamidate derivatives (*"Antisense RNA and DNA"*, WILLEY-LISS, 1992, pp. 1–50). Such chemically modified variant may be prepared according to, for example, the above-mentioned reference.

Such antisense oligonucleotides or chemically modified variants thereof may be used to control expression of the gene encoding tumor antigen protein. Since such control can decrease the amount of tumor antigen protein to be produced, and thereby decrease a damage caused by CTLs and also inhibit proliferation of CTL, autoimmune diseases due to over-expression of tumor antigen protein may be treated or prevented by such approach.

When the antisense oligonucleotides or chemically modified variants thereof are administered as such, preferred length thereof may be 8–200 bases, more preferably 10–25 bases, and most preferably 12–25 bases.

When inserted into expression plasmids, preferred length of the antisense oligonucleotides may be 100 bases or more, preferably 300–1000 bases, and more preferably 500–1000 bases.

Antisense oligonucleotides inserted in expression plasmids may be introduced into cells according to, for example, the methods described in *Jikken-Igaku*, vol. 12 (1994), such as those employing liposomes or recombinant viruses. Expression plasmids for antisense oligonucleotides may be easily prepared using conventional expression vectors just by placing the genes of the present invention after the promoter in the opposite direction so that the genes of the present invention may be transcribed in the direction from 3' to 5'.

When administered as such, antisense oligonucleotides or chemical variants of the antisense oligonucleotides may be formulated by mixing them with stabilizing agents, buffers, solvents, and/or the like, and then administered simultaneously with antibiotics, anti-inflammatory agents, or anesthetics. The formulations thus prepared may be administered via various routes. Such formulations are preferably administered everyday or every several days to every several weeks. Furthermore, in order to avoid such frequent administration, sustained-release minipellet formulation may also be prepared and implanted near the affected area. Alternatively, the formulation may be slowly administered in continuous manner using, for example, an osmotic pump. Dosage are typically to be adjusted so that the concentration at the site of action will be from 0.1 nM to 10 $\mu$M.

Tumor antigen proteins, tumor antigen peptides, and derivatives thereof having functionally equivalent properties, of the present invention may be used alone or in combination, and medicines comprising them as an active ingredient may be administered together with adjuvants or in particulate dosage form in order to effectively establish the cellular immunity. Specifically, when tumor antigen protein or tumor antigen peptide is administered to a subject, tumor antigen peptides are presented at high density on MHC class I antigens of the antigen-presenting cells, resulting in efficient proliferation of tumor-specific CTLs. For such purpose, those adjuvants described in the literature (*Clin. Microbiol. Rev.*, 7:277–289, 1994) are applicable. The active ingredient(s) are administered in a dosage form which allows the foreign antigen peptide to be efficiently presented on MHC class I antigen, such as liposomal preparations, particulate preparations in which the active ingredient(s) are bound to beads having a diameter of several $\mu$m, or preparations in which the active ingredient(s) are bound to lipids. It may be also possible to administer antigen-presenting cells such as dendritic cells or macrophages pulsed with the tumor antigen peptide, or cells transfected with DNA encoding the tumor antigen protein. Although the dose of the tumor antigen protein or tumor antigen peptide of the present invention in such preparations may be appropriately adjusted depending on various factors such as the disease to be treated, age and body weight of a particular patient, preferred dose is between 0.0001 mg and 1000 mg, and more preferably between 0.001 mg and 1000 mg. It is preferably administered every several days to every several months.

A method for in vitro induction of CTL from peripheral lymphocytes using tumor antigen peptide of the present invention is exemplified as follows.

Peripheral blood lymphocytes from an esophageal cancer patient with squamous cell carcinoma are in vitro-cultured, and a tumor antigen peptide of the present invention, for example, a peptide having the sequence of "736–744", "749–757", "785–793", or "690–698" is added to the culture medium at the final concentration of 10 $\mu$g/ml, in order to stimulate the peripheral blood lymphocytes. Such stimulation is repeated three times at intervals of one week. One week after the third stimulation, the peripheral blood lymphocytes are recovered, and measured for their cytotoxic activity according to the methods described in D. D. Kharkevitch et al, Int. J. Cancer, 58:317 (1994), in order to find CTL-inducing activity of the tumor antigen peptide of the present invention.

The method of the present invention for diagnosing tumors or autoimmune diseases may be conducted using antibodies specifically binding to a tumor antigen protein or tumor antigen peptide. Examples of such method may include those detecting tumor antigen protein in tumor tissue preparations, or detecting the presence of tumor antigen protein or antibodies against tumor antigen protein in blood or tissues. Such detection may be achieved by any appropriate method selected from, for example, immunohistochemical methods, immunoblotting, radioimmunoassay (RIA), enzyme-linked immunosorbent assay (ELISA), fluorescent and luminescent assays. Furthermore, detection of tumor antigen protein using antibodies enables early detection of tumors or their recurrence, as well as selection of patients who may be suitably treated with the tumor antigen proteins, tumor antigen peptides, or DNA encoding them.

BRIEF DESCRIPTION OF DRAWINGS

FIG. 1 is electrophoretograms showing the result of Northern blot hybridization described in Example 2.

In FIG. 1 a), KE-4, KE-3, TE-8, and TE-9 indicate esophageal cancer cell lines; Kuma-1 indicates a head and neck cancer cell line; HSC-4 indicates a mouth cancer cell line; Bec-1 indicates a B cell line; KMG-A indicates a gallbladder cancer cell line; R-27 indicates a breast cancer cell line; KIM-1, KYN-1, and HAK-3 indicate hepatic cancer cell lines; and M36 and M37 indicate melanoma cell lines.

EXAMPLES

The following detailed examples are presented by way of illustration of certain specific embodiments of the invention. The Examples are representative only and should not be construed as limiting in any respect.

Reference Example 1
Establishment of Cytotoxic T Lymphocyte (CTL) Cell Line against Esophageal Cancer Cell Line According to the disclosure of Nakao el al., *Cancer Res.*, 55:4248–4252 (1995), CTL against an esophageal cancer cell line, KE-4, belonging to squamous cell carcinomas when classified on the basis of the tissue type was established from peripheral blood monocytes of a patient, named KE-4CTL, and used in experiments. The esophageal cancer cell line KE-4 and KE-4CTL have been deposited at The National Institute of Bioscience and Human Technology (1-1-3 Higashi, Tsukuba, Ibaraki, Japan) under International Deposition Nos. FERM BP-5955 and FERM BP-5954, respectively, both on May 23, 1997. Furthermore, typing of HLA class I molecules of KE-4 was conducted according to the above-noted disclosure of Nakao et al., and it was confirmed that they are HLA-A2402, -A2601, B54, -B60, -Cw1, and -Cw3.

Reference Example 2
Preparation of HLA-A2061 cDNA and HLA-A2402 cDNA
Using KE-4, a recombinant plasmid was prepared by incorporating cDNA for HLA-A2601 into an expression vector pCR3 (INVITROGEN) according to the disclosure of Nakao et al., *Cancer Res.*, 55:4248–4252 (1995). Another recombinant plasmid for HLA-A2402 was also prepared in the similar manner.

Reference Example 3
Preparation of cDNA Library Derived from KE-4

Poly (A)+mRNA was prepared from KE-4 by isolation of total RNA fraction and purification on oligo (dT) column using mRNA Purification system (manufactured by Pharmacia Biotech) according to the manufacturer's protocol. cDNAs having Not I adapter and Sca I adapter linked to each terminus were prepared from mRNAs using SuperScript™ Plasmid System (Gibco BRL) according to the manufacturer's protocol, and then ligated to an expression vector, plasmid pSV-SPORT1 (Gibco BRL), digested with restriction enzymes Not I and Sal I, to yield recombinant plasmids. The recombinant plasmids were introduced into E. coli. ElectroMAX DH10B/p3™ T cells (Gibco BRL) using electric pulses in Gene Pulser (Bio-Rad) under conditions of 25 μF and 2.5 kV. Transformants into which the recombinant plasmids had been introduced were selected in LB medium (1% bacto-trypton, 0.5% yeast extract, 0.5% NaCl, pH7.3) containing ampicillin (50 μg/ml).

Reference Example 4
Quantitative Determination of Interferon-γ

Quantitative Determination of interferon-γ (IFN-γ) was conducted by enzyme immunoassay (ELISA). Anti-human IFN-γ mouse monoclonal antibody as a solid-phased antibody was adsorbed on wells of 96-well microplate, and after blocking non-specific bindings with bovine serum albumin, allowed to bind with IFN-γ in samples. Antihuman IFN-γ rabbit polygonal antibody as a detection antibody was then allowed to bind, and after binding with an anti-rabbit immunoglobulin goat antibody labeled with alkaline phosphatase, reacted with paranitrophenyl phosphate as a chromogenic substrate. After stopping the reaction by adding an equal volume of 1N NaOH, absorbance at 405 nm was measured. The absorbance was compared with that obtained with standard IFN-γ to determine the amount of IFN-γ in the sample.

Example 1
Screening of Gene for Novel Tumor Antigen Protein

The recombinant plasmid DNAs were recovered from pools of about 100 transformants described in Reference Example 3 as follows. A hundred transformants were introduced and cultured in each well of 96-well U-bottomed microplate containing LB medium plus ampicillin (50 μg/ml). Part of the culture was then transferred to another 96-well U-bottomed microplate containing 0.25 ml per well of TYGPN medium (F.M. Ausubel et al., *Current Protocols in Molecular Biology*, John Wiley & Sons, Inc.), and cultured for 48 hours at 37° C. The remaining cultures in LB medium on the microplate were stored in frozen. Preparation of recombinant plasmid DNAs from transformants cultured in TYGPN medium was achieved in the microplate by alkaline lysis (F.M. Ausubel et al., *Current Protocols in Molecular Biology*, John Wiley & Sons, Inc.). The recombinant plasmid DNAs recovered by isopropanol precipitation were suspended in 50 μl of 10 mM Tris, 1 mM EDTA, pH 7.4, containing 20 ng/ml RNase.

Fibroblast cell line, VA-13 cells (RIKEN CELL BANK, The Institute of Physical and Chemical Research; *Ann. Med. Exp. Biol. Fenn.*, 44:242–254, 1966) were doubly transfected with the recombinant plasmid for KE-4 cDNA and the recombinant plasmid for HLA-A2601 cDNA using Lipofectin method as follows. Seven thousands VA-13 cells were placed in each well of 96-well flat-bottomed microplate, and incubated for 2 days in 100 μl of RPMI 1640 medium containing 10% FCS. Using Lipofectin reagent (Gibco BRL), 30 μl of 70 μl mixture consisting of 25 μl of the recombinant plasmid for KE-4 cDNA corresponding to about 100 transformants, 10 μl (200 ng) of the recombinant plasmid for HLA-A2601 cDNA described in Reference Example 2, and 35 μl of about 35-fold diluted Lipofectin reagent was added to VA-13 cells to be doubly transfected. Transfectants were prepared in duplicate. After 5 hours, 200 μl of culture medium containing 10% FCS was added to the transfectants, and further incubated for 72 hours at 37° C. After removing the culture medium, 10,000 KE-4CTL cells were added to each well, and cultured for 24 hours at 37° C in 100 μl of culture medium containing 10% FCS and 25 U/ml IL-2. The culture medium was recovered, and measured for IFN-γ by ELISA.

Regarding four groups in which high production of IFN-γ was observed, corresponding frozen-stored pools of about 100 transformants containing recombinant plasmids for KE-4 cDNA were used in the following screening. The pools of the transformants were plated on LB agar medium containing ampicillin (50 μg/ml) to obtain colonies. Two hundreds colonies for each group (total 800 colonies) were cultured as described above so that a single kind of transformant is included in each well, thereby recombinant plasmid DNAs for KE-4 cDNA were prepared. Then, VA-13 cells were doubly transfected with the recombinant plasmid for KE-4 cDNA and the recombinant plasmid for HLA-A2601 cDNA followed by cocultivation with KE-4CTL, and IFN-γ produced due to KE-4CTL reaction was quantitatively determined as described above in order to select positive plasmids. In this manner, a single KE-4 cDNA recombinant plasmid clone was selected and named 6DI. Furthermore, similar procedures were repeated with 6DI to determine the amount of IFN-γ produced by KE-4CTL according to the method described in Reference Example 4. The results are shown in the following TABLE 1.

TABLE 1

| Target cell | Amount of IFN-γ produced by KE-4CTL (pg/ml) |
|---|---|
| VA-13 cell | 0 |
| VA-13 cell + HLA-A2601 | 1.8 |
| VA-13 cell + 6DI | 4.3 |
| VA-13 cell + HLA-A2601 + 6DI | 24.0 |
| VA-13 cell + HLA-A0201[1)] | 0.9 |
| VA-13 cell + HLA-A0201 + 6DI[1)] | 3.0 |

[1)]For comparison, HLA of different type was transfected.
(These date was obtained by transfection using the following amounts of DNA: 200 ng of HLA-A2601 or HLA-A0201, 100 ng of 6DI.)

Figure 1A:
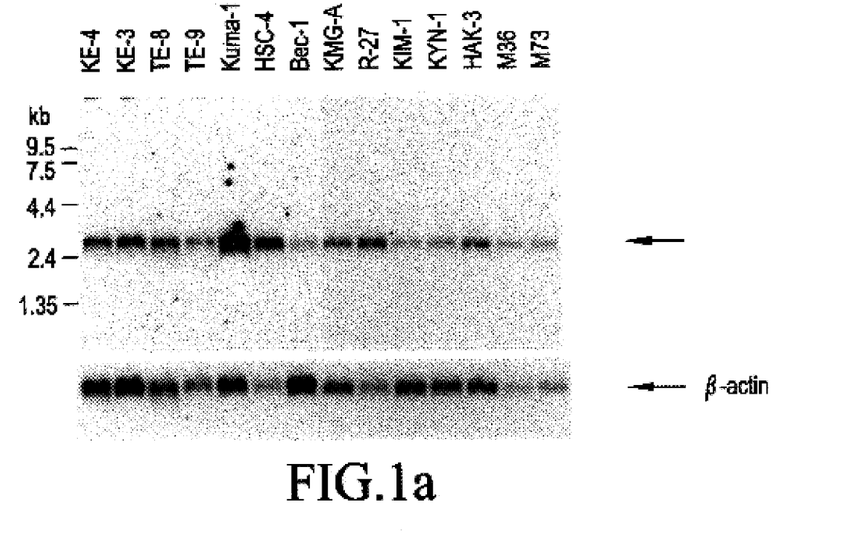
Figure 1B:
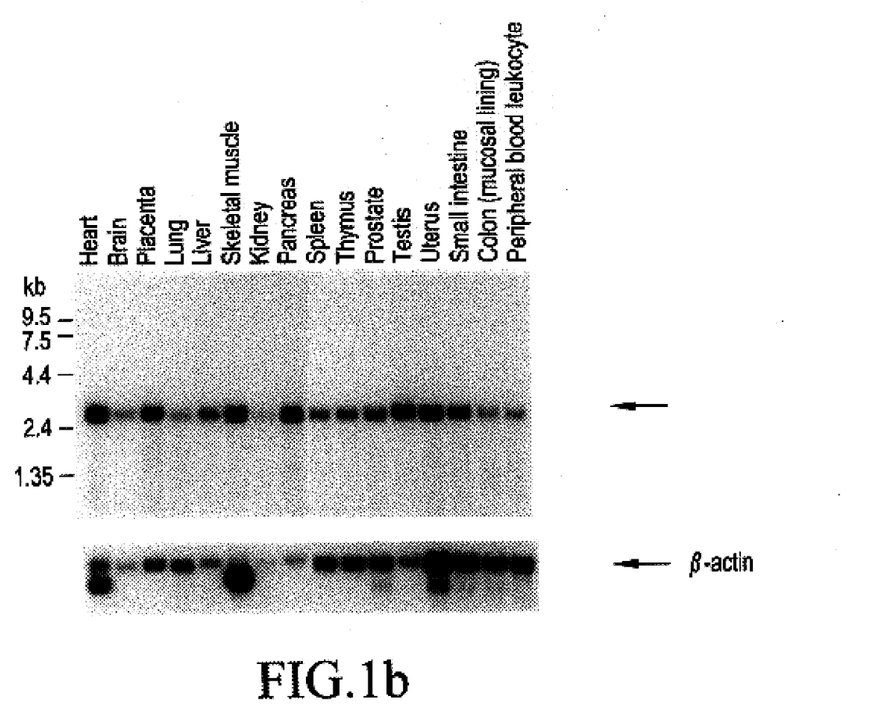

Example 2
Expression Analysis for Tumor Antigen Protein Gene by Northern Hybridization RNAs were prepared from various cell lines using RNAzol B (TEL-TEST, Inc.). Five μg of RNA was denatured in the presence of formamide and formaldehyde, electrophoresed on agarose, then transferred and fixed onto Hybond-N+ Nylon membrane (Amersham). As RNAs from normal tissues, commercially available membranes (Clontech) onto which mRNAs have been preblotted were used. The inserted sequence region of the recombinant plasmid 6DI cloned in Example 1 was labeled with $^{32}P$ using Multiprime DNA labelling system (Amersham) to prepare DNA probe. According to the known method (Nakayama el al., *Bio-Jikken-Illustrated*, vol. 2, "Idenshi-Kaiseki-No-Kiso (A Basis for Gene Analysis)", pp. 148–151, Shujunsha, 1995), this probe was hybridized to RNAs on the membranes, and subjected to autoradiography to detect mRNA for tumor antigen protein gene of the present invention. The membranes used for the detection of mRNA for said gene were boiled in 0.5% aqueous sodium dodecyl sulfate to remove the probe, and subjected to Northern hybridization in a similar manner using β-actin as a probe which is constitutively expressed in cells, in order to detect mRNA which was used as an internal standard. The results are shown in FIG. 1. It became apparent from these results that mRNA for tumor antigen protein gene of the present invention is widely expressed in various cancer cells and normal tissues, and is about 2.5 kb in full length (FIG. 1).

Example 3
Cloning and Base Sequencing of Full-Length cDNA Clone Encoding Tumor Antigen Protein KE-4-derived cDNA Library described in Reference Example 3 was plated on LB agar medium containing ampicillin (50 μg/ml). The colonies thus obtained were then transferred and fixed on Hybond-N+ nylon membrane (Amersham) according to the manufacturer's protocol. The same 6DI probe as that used in Example 2 was employed for hybridization and autoradiography under the same conditions as those used in Example 2, in order to select colonies which contain recombinant plasmids having the cDNA for tumor antigen protein gene incorporated. Furthermore, recombinant plasmids were recovered from the colonies selected, treated with restriction enzymes Not I and Sal I, and then electrophoresed on agarose to determine the length of incorporated cDNAs. A recombinant plasmid incorporating cDNA of about 2.5 kb was selected, and named K3. The base sequence of the cDNA region in this plasmid K3 was determined using DyeDeoxy Terminator Cycle Sequencing kit (Perkin-Elmer). The base sequence thus determined is shown in SEQ ID NO: 1. The full-length of the cDNA was 2527 base pairs. The amino acid sequence (800 amino acids) encoded by the base sequence of SEQ ID NO: 1 is shown in SEQ ID NO: 2.

The analysis indicated that the base sequence shown in SEQ ID NO: 1 does not show homology with known tumor antigen protein genes derived from melanomas and thus proved to be a different gene. The search for the base sequence of SEQ ID NO: 1 using WWW Entrez database revealed that part of the base sequence of the present invention exhibits high homology more than 90% to three gene sequences, functions of which are not known, decoded by WashU-Merck EST Project and registered at GENBANK under Accession Nos. R89163, R62890, and R00027. No. R89163 corresponds to the sequence of positions 1893–2267; R62890 corresponds to the sequence of positions 2018–2389; and R00027 corresponds to the sequence of positions 2024–2510. These sequences correspond, however, to the base sequences 3' to the initiation codon in the base sequence of the present invention, and therefore, the amino acid sequences they encode can not be determined.

After determination of the base sequence as described above, the plasmid K3 was introduced into E. coli JM109 to obtain E. coli JM109(K3) which is a transformant for storage containing the novel tumor antigen protein cDNA of the present invention. E. coli JM109(K3) has been deposited at The National Institute of Bioscience and Human Technology (1-1-3 Higashi, Tsukuba, Ibaraki, Japan) under International Deposition No. FERM BP-5951 on May 22, 1997.

Furthermore, CDNA library derived from normal human tissue (peripheral blood lymphocyte) was also screened in the manner as described above. This screening resulted in cloning of a recombinant plasmid into which cDNA of about 2.5 kb has been incorporated. It was found by determining the base sequence of this cDNA that cDNA thus cloned was the same as that shown in SEQ ID NO: 1 except for position 812 (position 812 for normal human tissue was T). It was thus indicated that in connection with the full-length gene comprising the gene encoding the tumor antigen protein of the present invention, almost the same genes are expressed in both cancer cells and normal human tissue.

VA-13 Cells were then doubly transfected with the recombinant plasmid K3 incorporating cDNA for the novel tumor antigen protein gene and another recombinant plasmid incorporating cDNA for HLA-A2601, and used as target cells. The amount of IFN-γ produced by the reaction of KE-4CTL was determined according to the method described in Reference Example 4. The results are shown in the following TABLE 2.

TABLE 2

| Target cell | Amount of IFN-γ produced by KE-4CTL[1] (pg/ml) |
| --- | --- |
| VA-13 cell + HLA-A2601 + K3 | 1439 |
| VA-13 cell + HLA-A0201[2] + K3 | 10 |

[1]Values obtained by subtracting the amount (background) of IFN-γ produced by KE-4CTL in response to VA-13 cells transfected with each HLA.
[2]For comparison, HLA of different type was transfected.
(These date was obtained by transfection of the following amounts of DNA: 200 ng of HLA-A2601 or HLA-A0201, 100 ng of K3.)

Example 4
Identification of Tumor Antigen Peptide

From the recombinant plasmid 6DI cloned in Example 1 which incorporated partial cDNA for the novel tumor antigen protein gene, plasmids containing partial cDNA for tumor antigen protein gene of various length were prepared using Deletion Kit for Kilo-Sequence (Takara Shuzo Co.) according to the manufacturer's protocol. These plasmids were introduced into E. Coli ElectroMax DH10B/p3™ cells (Gibco BRL). The cells were plated on agar medium, and 50 colonies were selected at random. From the colonies, plasmid DNAs were prepared, subjected to electrophoresis, and 5 clones which contained plasmids having appropriate length selected.

According to the method described in Example 1, VA-13 cells were doubly transfected with HLA-A2601 cDNA and the above plasmid DNA, cocultured with KE-4CTL, and IFN-γ in the culture medium was quantitatively determined according to the method described in Reference Example 4. As a result, it was found that the transfectant with a plasmid lacking the base sequence after position 2253 in SEQ ID No: 1 had no IFN-γ-inducing activity on KE-4CTL. It was therefore suggested that peptides having the sequence after about position 739 in the amino acid sequence of SEQ ID NO: 2 may have IFN-γ-inducing activity on KE-4CTL.

Thus, a series of 21 different peptides each consisting of successive 10 amino acid residues in the amino acid sequence after position 730 in SEQ ID NO: 2 were synthesized so that they each have the amino acid sequence shifted serially by three amino acid residues. Using these peptides, IFN-γ in culture medium was determined as described above except that the antigen presentation was achieved by pulsing HLA-A2601 cDNA-transfected VA-13 cells with the peptides. As the result, IFN-γ-inducing activity was observed in the peptides having the amino acid sequences of "736–745", "748–757", and "784–793" in SEQ ID NO: 2.

For each of these three peptides, additional peptides consisting of 9 amino acid residues were synthesized by truncating the N- or C-terminal residue, and used for measurement of IFN-γ-inducing activity in a similar manner. Stronger IFN-γ-inducing activity was observed for the peptides having the amino acid sequences of "736–744", "749–757", and "785–793" in SEQ ID NO: 2. The results are shown in TABLE 3.

TABLE 3

| Pulsed cell | Peptide | Amount of INF-γ produced by KE4-CTL cells (pg/ml) |
|---|---|---|
| VA-13/A2601[1] | "736–744" | 203 |
| VA-13/A0201[2] | "736–744" | 44 |
| VA-13/A2601 | "749–757" | 183 |
| VA-13/A0201 | "749–757" | 89 |
| VA-13/A2601 | "785–793" | 394 |
| VA-13/A0201 | "785–793" | 102 |

[1]VA-13 cells transfected with HLA-A2601 cDNA
[2]VA-13 cells transfected with different HLA-0201 cDNA as a control The results in TABLE 3 suggest that these peptides function as a tumor antigen peptides.

In addition, it is known that there are certain rules (motifs) in the sequences of antigen peptides bound and presented by HLA molecules. Concerning the motif for HLA-A24, the second amino acid is tyrosine and the ninth amino acid is isoleucine, leucine or phenylalanine in the sequence of antigen peptides consisting of 9 amino acid residues (*Immunogenetics*, 41:178–228, 1995).

Thus, another peptide having the amino acid sequence of "690–698" in SEQ ID NO: 2 which corresponds to the above motif was further synthesized. VA-13 cells transfected with HLA-A2402 cDNA was then pulsed with the peptide, and IFN-γ-inducing activity on KE4CTL was measured as described above. The results are shown in TABLE 4.

TABLE 4

| Pulsed cell | Peptide | Amount of INF-γ produced by KE4-CTL cells (pg/ml) |
|---|---|---|
| VA-13 | "690–698" | 157 |
| VA-13/A2402[1] | "690–698" | 269 |
| VA-13/A0201[2] | "690–698" | 166 |

[1]VA-13 cells transfected with HLA-A2402 cDNA
[2]VA-13 cells transfected with different HLA-A0201 cDNA as a control The results in TABLE 4 suggest that the peptide "690–698" functions as a tumor antigen peptide.

Example 5
Inducement of CTL from peripheral blood lymphocytes by tumor antigen peptides The inventors have investigated whether antigen-specific CTL can be induced from peripheral blood lymphocytes of the cancer patient from whom KE-4 was derived, by in vitro stimulation with the tumor antigen peptides described in Example 3. Tumor antigen peptides used were those peptides having the sequences of "736–744", "749–757", and "690–698", obtained in the above Example 3. Frozen peripheral blood lymphocytes, which had been separated from the above cancer patient using Ficoll method, were awoke, transferred to 24-well plate at about 2×10$^6$ cells/well, and cultured in RPMI 1640 medium containing 10% FCS and IL-2 (100 U/ml). To stimulate the peripheral blood lymphocytes, the above tumor antigen peptide was added to the culture medium at 10 μg/ml. After one week, 10 μg/ml of the above tumor antigen peptide was added together with about 1×10$^5$ cells of X ray-radiated (50 Gy) peripheral blood lymphocytes for the second stimulation. After additional one week, the third stimulation was conducted in a similar manner.

For peptides having the sequences of "736–744" and "749–757", peripheral blood lymphocytes were recovered one week after the third stimulation, and measured for their cytotoxic activity using, as target cells, $^{51}$Cr-labeled KE-4 and another esophageal cancer cell line KE-3 of which HLA-A loci are A2402 and A2, according to the method described in D.D. Kharkevitch et al., *Int. J. Cancer*, 58:317 (1994). The results are shown in TABLE 5.

TABLE 5

| Effector cell | Target cell | Toxic activity (%) |
|---|---|---|
| Peripheral blood lymphocytes stimulated with "736–744" | KE-4 | 22.1 |
| | KE-3 | 3.7 |
| Peripheral blood lymphocytes stimulated with "749–757" | KE-4 | 35.9 |
| | KE-3 | 24.2 |

When stimulated with the peptide having the sequence of "736–744", KE-4 was severely injured, whereas the negative control KE-3 was not injured. It was therefore demonstrated that CTL specific for KE-4 was induced. Similarly, when stimulated with the peptide having the sequence of "749–757", stronger cytotoxic activity was observed on KE-4, although nonspecific cytotoxic activity was also observed on KE-3, suggesting that CTL specific for KE-4 was induced.

For peptide having the sequence of "690–698", peripheral blood lymphocytes were recovered after the third stimulation, and further cultured in RPMI-1640 medium containing 10% FCS, 50% AIM-V (Gibco BRL), and IL-2 (100 U/ml). Then, the cytotoxic activity was measured as above using $^{51}$Cr-labeled KE-4 and VA-13 cells as target cells. In addition, lymphocytes were isolated from peripheral blood of a normal individual of which HLA-A loci were homozygous A24, and measured for their cytotoxic activity in the same manner as above using, as target cells, $^{51}$Cr-labeled KE-4 and lung cancer cell line QG-56 of which HLA-A loci are homozygous A2601. The results are shown in TABLE 6.

TABLE 6

| Effector cell | Target cell | Toxic activity (%) |
|---|---|---|
| "690–698"-Stimulated peripheral blood lymphocytes from a cancer patient | KE-4 | 24.7 |
| | VA-13 | 13.8 |
| "690–698"-Stimulated peripheral blood lymphocytes from a normal individual | KE-4 | 17.7 |
| | QG-56 | 11.5 |

By stimulating peripheral blood lymphocytes from a cancer patient and from a normal individual with the peptide having the sequence of "690–698", stronger cytotoxic activity was observed on KE-4, although nonspecific cytotoxic activity was also observed on the negative controls VA-13 and QG-56 cells. The above results suggest that CTLs specific for KE-4 were induced.

Effects of the Invention

According to the present invention, there are provided medicines for activating antitumor immunity by means of tumor antigen proteins and tumor antigen peptides, medicines for treating autoimmune diseases, and medicines comprising DNA or the like encoding tumor antigen protein, as well as methods for diagnosing tumors or autoimmune diseases.

What is claimed is:

1. An isolated tumor antigen protein selected from the group consisting of:
   (a) a protein comprising an amino acid sequence shown in SEQ ID NO:2; and
   (b) a protein encoded by a DNA comprising a nucleotide sequence shown in SEQ ID NO:1,
   wherein said protein yields, through intracellular decomposition, peptide fragment(s) which binds to major histocompatibility complex (MHC) class I antigen and is recognized by tumor-specific cytotoxic T lymphocytes (CTLs) in such binding state.

2. An isolated and chemically synthesized tumor antigen peptide that is a peptide fragment of a tumor antigen protein selected from the group consisting of:
   (a) a protein comprising an amino acid sequence shown in SEQ ID NO:2; and
   (b) a protein encoded by a DNA comprising a nucleotide sequence shown in SEQ ID NO:1,
   wherein said tumor antigen peptide comprises the amino acid sequence of positions 749–757, 736–744, 785–793, or 690–698 in the amino acid dequence of SEQ ID NO:2, and binds to MHC class I antigen and is recognized by tumor-specific CTLs when bound to MHC class I antigen.

3. A composition comprising, as an active ingredient, the tumor antigen protein of claim 1.

4. A composition comprising, as an active ingredient, the tumor antigen peptide of claim 2.

* * * * *

UNITED STATES PATENT AND TRADEMARK OFFICE
CERTIFICATE OF CORRECTION

PATENT NO. : 6,815,531 B1
DATED : November 9, 2004
INVENTOR(S) : Kyogo Itoh et al.

It is certified that error appears in the above-identified patent and that said Letters Patent is hereby corrected as shown below:

Title page,
Item [30], Foreign Application Priority Data, please correct as follows:
-- [30] Foreign Application Priority Data
    Jun. 7, 1996    (JP) ……………………..8-168429
    Oct. 8, 1996    (JP) ……………………..8-287572
    Nov. 25, 1996    (JP) ……………………..8-330424 --

Signed and Sealed this

Twenty-fourth Day of May, 2005

JON W. DUDAS
*Director of the United States Patent and Trademark Office*